United States Patent [19]
Green et al.

[11] 4,025,627
[45] May 24, 1977

[54] MICROBIOCIDAL POLYMERIC QUATERNARY AMMONIUM COMPOUNDS

[75] Inventors: Harold A. Green, Havertown, Pa.; John J. Merianos, Jersey City; Alfonso N. Petrocci, Glen Rock, both of N.J.

[73] Assignee: Millmaster Onyx Corporation, New York, N.Y.

[22] Filed: Apr. 7, 1975

[21] Appl. No.: 565,839

Related U.S. Application Data

[60] Division of Ser. No. 478,524, June 12, 1974, which is a continuation-in-part of Ser. No. 425,931, Dec. 18, 1973, Pat. No. 3,874,870.

[52] U.S. Cl. .......................... 424/248.4; 424/244; 424/250; 424/267
[51] Int. Cl.² ........................................... A01N 9/22
[58] Field of Search .................. 424/248, 267, 250; 260/246 B

[56] References Cited
UNITED STATES PATENTS

| | | | |
|---|---|---|---|
| 2,716,134 | 8/1955 | Reynolds et al. | 260/246 B |
| 3,371,116 | 2/1968 | Nordgren et al. | 260/567.6 P |

OTHER PUBLICATIONS
Chemical Abstracts, vol. 69 (1968), p. 2504r.

*Primary Examiner*—V. D. Turner
*Attorney, Agent, or Firm*—Arthur A. Jacobs

[57] ABSTRACT

Microbiocidally active compounds comprising the condensation products of 1,4-dihalo-2-butene and difunctional tertiary amines of the type:

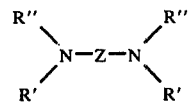

wherein Z is a cyclic or acyclic divalent aliphatic radical of 2 to 10 carbon atoms which may contain 0 to 2 double bonds or 0 to 2 hydroxy substituents; and wherein R' and R" are either the same or different and where they may be either (a) primary or secondary alkyls having 1 to 20 carbon atoms with a total sum of no greater than 36 carbon atoms, (b) hydroxy or dihydroxy derivatives of the aforesaid primary or secondary alkyls, (c) benzyl, (d) alkyl-benzyl, or (e) combined with N to form a heterocyclic group.

3 Claims, No Drawings

MICROBIOCIDAL POLYMERIC QUATERNARY AMMONIUM COMPOUNDS

This is a division of co-pending application Ser. No. 478,524, filed June 12, 1974, which is in turn a continuation-in-part of co-pending application Ser. No. 425,931, filed Dec. 18, 1973, now U.S. Pat. No. 3,874,870.

As set forth in the aforesaid parent application, it was discovered that the condensation products of 1,4-dihalo-2-butene and 1,4-bis-dimethylamino-2-butene were highly effective microbiocidal agents in aqueous systems, particularly in recirculating and industrial waters as well as in emulsions containing non-ionic emulsifiers, and particularly cosmetic emulsions, both of the water-in-oil and oil-in-water type. It was further, disclosed that the aforesaid microbiocidal action was effected without undue foaming. A particular aspect of such compounds is that the quaternary ammonium moieties thereof are part of a long chain rather than part of a chain bonded to the long chain.

It has now been discovered, in accordance with the present invention, that similar biocidal activity is obtained with compounds prepared as the condensation products of 1,4-dihalo-2-butene and other diamines, more particularly, di-functional tertiary amines of the type:

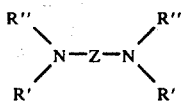

wherein Z is a divalent aliphatic radical of 2 to 10 carbon atoms which may contain 0 to 2 double bonds or 0 to 2 hydroxy substituents; wherein R' and R'' are either the same or different and wherein they may be: (a) primary or secondary alkyls having from 1 to 20 carbon atoms, where the sum of the carbon atoms in R' and R'' is no greater than 36 and where such sum is at least 3 when Z is $-CH_2-CH=CH-CH_2$, (b) hydroxy or dihydroxy derivatives of the primary or secondary alkyl radicals described in (a), (c) benzyl, (d) benzyl having at least one alkyl group attached to the benzene ring, where the total number of carbon atoms in the alkyl groups attached to the benzene ring is less than 7, or (e) combined with N wherein

may be a heterocyclic group such as N-piperidino, N-pyrrolidino N-morpholino or N-homopiperidino.

Exemplary of such difunctional tertiary amines are N,N'-di-lower alkyl piperazine and 1,4-diazabicyclo (2.2.2) octane.

There is no absolute certainty of the actual structure of the product of the condensation reaction because of possible isomerizations; however, ideally, the reaction would appear to be exemplified by the following, wherein Z, R' and R'' are the same as in the formula above, wherein X is a halogen such as chlorine or bromine, and wherein n is an integer of from about 2 to about 30:

n XCH$_2$—CH=CH—CH$_2$—X + n R'R''N—Z—NR'R''

When Z is the divalent organic radical $-CH_2-CH=CH-CH_2-$, the reaction may be represented as follows:

n X—CH$_2$—CH=CH—CH$_2$—X + n R'R''N—CH$_2$CH=CH—CH$_2$—NR'R''

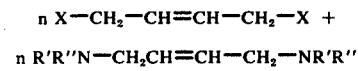

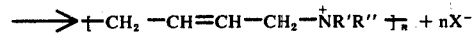

where the meaning of each symbol is the same as that described above.

Although some of the aforesaid compounds are active against *Pseudomonas aeruginosa* and *Aerobacter aerogenes* at a concentration as low as 25 ppm, relative to the total composition, the preferred range is about 50–100 ppm. Insofar as concerns the upper limits, the concentration appears capable of being increased indefinitely without deleteriously affecting the biocidal activity.

With regard to cosmetic compositions, at least some of the products are effective at a concentration as low as about 500 ppm, or probably even lower, although the preferred range is about 1,000 to about 2,000 ppm. Furthermore, when non-ionic emulsifiers, such as are generally used in cosmetic compositions, are present, there is no significant diminution of the biocidal effectivenss of the microbiocidal products of this invention.

The following examples illustrate the present invention:

EXAMPLE 1

522 grams of morpholine (6 moles) were cooled to 20° C and 125 grams of 1,4-dichloro-2-butene (1 mole) were added dropwise with constant stirring and cooling to keep the temperature at 50° C–60° C. The entire addition took about 1 hour, and stirring was continued for about 1 hour. While stirring, 150 grams of water was poured into the reaction mixture, followed by 200 grams of 50% sodium hydroxide solution, then the mixture was allowed to separate.

The organic layer was removed, and the unreacted morpholine was removed by distillation under reduced pressure. The residue was washed with water and filtered, yielding a yellow solid melting at 79° C–83° C. This was 1,4-bis-(N-morpholino)-2-butene.

Since the purpose of the excess morpholine was to act as an acid acceptor, the experiment was repeated, but with 212 grams of sodium carbonate (2 moles) replacing the excess 174 grams or morpholine (4 moles). The yield of 1,4-bis-(N-morpholino)-2-butene was about the same as the previous synthesis.

This reaction was repeated using 0.1 mole of 1,4-dichloro-2-butene and -.6 mole of the following amines in place or morpholine: piperidine, homopiperidine, diethanolamine, dimethylamine, dipropylamine, dibutylamine, di-(2-ethylhexyl) amine, dioctylamine, didecylamine, didodecylamine, N-methyl propylamine, N-methyl butylamine, N-methyl hexaylamine, N-methyl octylamine, N-methyl decylamine, N-methyl dodecylamine. All of these 1,4-bis-amine-2-butenes were liquids, and were recovered from their aqueous mixtures by partitioning.

EXAMPLE 2

22.6 grams of 1,4-bis-(N-morpholine)-2-butene (0.1 mole) was suspended in 25 grams of water, and to it was addd dropwise, with constant stirring, 12.5 grams of 1,4-dichloro-2-butene (0.1 mole) at a rate which kept the reaction temperature between 60° C and 70° C. The addition took about 15–30 minutes. Then the reaction mixture was stirred for about 1 hour on a steam bath at about 80° C at which time analysis for ionic chloride showed that the reaction was about 98%–100% complete. The reaction product was a viscous material containing about 55% of active polyquaternary compound. When an excess of an organic solvent; i.e. an alcohol such as isopropanol or a ketone such as acetone, was added to the aqueous solution, the polyquaternary product precipitated and was separated by filtration.

Quite surprisingly, when organic solvents such as isopropanol, acetone, or inert halogenated solvent such as 1,1,1-trichloroethane were used instead of water as the reaction solvent, the polymeric quaternary product precipitated out of the reaction mixture as a solid, and was separated by filtration.

This same procedure was followed, using each of the other di-tertiary amines made in Example 1, instead of 1,4-bis-(N-morpholine)-2-butene. In addition to the 1,4-ditertiaryamino-2-butenes described in Example 2, other di-tertiary amines were reacted with 1,4-dichloro-2-butene to produce polyquaternary compounds, as shown by the following examples:

EXAMPLE 3

11.4 grams of 1,4-N,N'-dimethylpiperazine (0.1 mole) was suspended in 25 grams of water and to it was added dropwise, with constant stirring, 12.5 grams of 1,4-dichloro-2-butene (0.1 mole) at a rate which kept the reaction temperature between 60° C and 70° C. The addition took about 15–30 minutes. Then the reaction mixture was stirred for about 1 hour on a steam bath at about 80° C at which time analysis for ionic chloride showed that the reaction was about 98%–100% complete. The reaction product was a viscous material containing about 45% of active polyquaternary compound. When an excess of an organic solvent such as isopropanol or acetone was added to the aqueous solution, the polyquaternary product precipitated, and was separated by filtration.

Here, too, when organic solvents such as isopropanol, acetone, or 1,1,1-trichloroethane were used instead of water as the reaction solvent, the polymeric quaternary product precipitated out of the reaction mixture as a solid, and was separated by filtration.

EXAMPLE 4

The procedure of Example 3 was repeated using 0.1 mole of the following di-tertiary amines instead of N,N'-dimethyl piperazine; 1,4-diazobicyclo (2.2.2) octane; N,N,N',N'-tetra-methylethylene diamine; NNN'N'-tetra-(2-hydroxypropyl) ethylene diamine; 1,3-bis-(dimethylamino)-2-hydroxypropane.

As stated above, the exact structure of the polyquaternary ammonium salts prepared in the above manner cannot be determined with complete certainty, but it is these products which provide the functional characteristics which are here desired. Therefore, in order to determine if products of this type, prepared in another manner, also function for the same purposes, one-step reactions were used whereby 2 moles of a secondary amine and one mole of 1,4-dichloro-2-butene were used, the secondary amine being morpholine in one instance and dimethylamine in the other instance. Ideally, this reaction may be represented by the following equation:

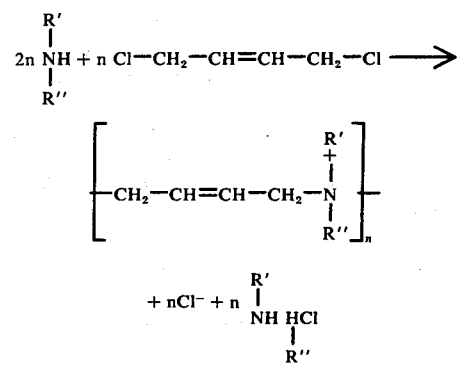

Since one mole of secondary amine was used as an acid acceptor, the reaction product contained, as an impurity, the hydrochloride salt of the secondary amine. In order to purify the polyquaternary salt, the secondary amine was liberated from its salt by adding sodium hydroxide and extracted with ether.

In a modification of this one-step synthesis, one mol of sodium hydroxide replaced one mol of secondary amine as an acid acceptor.

Both modifications of the one-step synthesis contained sodium chloride as an impurity which could not be easily or satisfactorily removed from the polyquaternary product. Furthermore, the products obtained by these two modified processes had unsatisfactory coloration and viscosities, so that they could not be satisfactorily used for cosmetics and related fields.

In order to test the biocidal and foaming properties of this invention, the following representative products were chosen for each test:

a. The polyquaternary ammonium product formed by the condensation of 1,4-dichloro-2-butene with 1,4-diazabicyclo (2.2.2) octane in approximately equimolar proportions.

b. The polyquaternary ammonium product formed by the condensation of 1,4-bis-(N-morpholino)-2-butene with 1,4-dichloro-2-butene in approximately equimolar proportions.

c. The polyquaternary ammonium product formed by the condensation of 1,4-dichloro-2-butene with 1,4-di(N-homopiperidino)-2-butene in approximately equimolar proportions.

d. The polyquaternary ammonium product formed by the condensation of 1,4-dichloro-2-butene with 1,3-bis-(dimethylamino)-2 hydroxy propane in approximately equimolar proportions.

e. The polyquaternary ammonium product formed by the condensation of 1,4-dichloro-2-butene with NNN'λ N'-tetra-(2 hydroxypropyl)-ethylene diamine in approximately equimolar proportions.

f. The polyquaternary ammonium product formed by the condensation of 1,4-dichloro-2-butene with N,N'-dimethylpiperazine in approximately equimolar proportions.

EXAMPLE 5

Each potential bactericidal compound to be tested (i.e. compounds (a), (b), (c), (d), (e) and (f) of Example 4) was dissolved in distilled water to the test concentration, and 50 ml. was added aseptically to previously sterilized cotton-stoppered 125 ml. Erlenmeyer flasks. One set of test flasks containing the potential bactericide at concentrations of 25 ppm., 50 ppm., 100 ppm., 150 ppm., 200 ppm., 250 ppm., 300 ppm., was inoculated by introducing into each flask 0.5 ml. of a 1/10 nutrient broth dilution of a 24-hour nutrient broth culture of Aerobacter aerogenes. Another set of test flasks containing the potential bactericide at the same concentrations was inoculated by introducing into each flask 0.5 mo. of a 1/10 nutrient broth solution of a 24-hour nutrient broth culture of Pseudomonas aeruginosa.

At intervals of 30, 60, and 180 minutes following inoculation, a 1 ml. aliquot was withdrawn from each flask and added to 9 ml. of sterile azolectin/"Tween 80" neutralizer from which additional tenfold serial dilutions were prepared in the sterile neutralizer solution.

Nutrient agar plates were prepared from $1 \times 10^{-2}$ and $1 \times 10^{-3}$ dilutions.

Simultaneously with each set of test flasks, a control of sterile distilled water was similarly inoculated, and aliquots were made at the same time intervals and plates at $1 \times 10^{-4}$, $1 \times 10^{-5}$ and $1 \times 10^{6}$ dilutions.

A comparison of the surviving organisms for various test concentrations of the test material at different time intervals was made and tabulated.

The results were as follows:

TABLE 1

Number of survivors of *P. aeruginosa* ATCCNo.15442 following exposure to the various polyquaternary compounds at different concentrations for various periods of time:

| Compound | Concentration in ppm. | No. of Bacteria/ml. × 10² after 30 min. | 60 min. | 180 min. |
|---|---|---|---|---|
| (a) | 25 | 126 | 27 | <1 |
| | 50 | 67 | 9 | <1 |
| | 100 | <1 | <1 | <1 |
| (b) | 50 | 301 | 156 | <1 |
| | 100 | 78 | 17 | <1 |
| | 200 | <1 | <1 | <1 |
| (c) | 50 | 160 | 21 | 4 |
| | 100 | 67 | 6 | <1 |
| | 200 | <1 | <1 | <1 |
| (d) | 25 | 102 | 36 | <1 |
| | 50 | 61 | <1 | <1 |
| | 100 | <1 | <1 | <1 |
| (e) | 200 | 300 | 233 | 114 |
| | 250 | 157 | 48 | 7 |
| | 300 | 72 | 19 | <1 |
| (f) | 25 | 51 | 13 | <1 |
| | 50 | 17 | <1 | <1 |
| | 100 | <1 | <1 | <1 |
| (g) Control | 0 | 61,000 | 139,000 | 270,000 |

TABLE 2

Number of survivors of *A. aerogenes* following exposure to the various polyquaternary compounds at different concentrations for various periods of time:

| Compound | Concentration in ppm. | No. of Bacteria/ml. × 10² after 30 min. | 60 min. | 180 min. |
|---|---|---|---|---|
| (a) | 25 | 55 | 10 | <1 |
| | 50 | 30 | <1 | <1 |
| | 100 | <1 | <1 | <1 |
| (b) | 50 | 167 | 57 | <1 |
| | 100 | 71 | 17 | <1 |
| | 150 | 8 | <1 | <1 |
| (c) | 100 | 180 | 62 | 1 |
| | 150 | 97 | 26 | 1 |
| | 200 | 1 | 1 | 1 |
| (d) | 100 | 77 | 22 | 1 |
| | 150 | 35 | 10 | 1 |
| | 200 | 1 | 1 | 1 |
| (e) | 200 | 173 | 68 | 7 |
| | 250 | 68 | 19 | 1 |
| (f) | 25 | 70 | 23 | 1 |
| | 50 | 26 | 3 | 1 |
| | 100 | 1 | 1 | 1 |
| (g) Control | 0 | 109,500 | 151,000 | 236,500 |

Table 3

Concentrations in ppm, at which the polyquaternary ammonium polyelectrolytes demonstrate highly effective reduction of bacteria:

| Compound | Pseudomonas aeroginosa | Aerobacter aerogenes |
|---|---|---|
| (a) | 25 – 50 | 25 – 50 |
| (b) | 50 – 100 | 100 |
| (c) | 50 | 100 – 150 |
| (d) | 25 – 50 | 100 |
| (e) | 250 – 300 | 200 |
| (f) | 25 – 50 | 25 |

EXAMPLE 6

In order to determine the foaming properties of the products of the present invention, the standard Ross-Miles test was performed on the representative products. The procedure that was used is the one reported in "ASTM STANDARDS", Designation 1175-53, Part X, page 878, which is the ASTM test for foaming properties of surface active materials. The results were as follows:

Table 4

Distilled water at 40° C (104° F)
Sampel at 50 ppm.

| Product | Solution Clarity | Foam Height in mm. 0 min. | 1 min. | 5 min. |
|---|---|---|---|---|
| (a) | Clear | 0 | 0 | 0 |
| (b) | Clear | 0 | 0 | 0 |
| (c) | Clear | 0 | 0 | 0 |
| (d) | Clear | 0 | 0 | 0 |
| (e) | Clear | 0 | 0 | 0 |
| (f) | Clear | 0 | 0 | 0 |

Another test used was the "Waring Blender Foam Test". The procedure is as follows: A graduated blender cylinder is rinsed with distilled water. 100 ml. of aqueous test solution is added down the walls of the blender so as to cause no foam. The blender is turned to high speed for exactly 5 seconds, and upon turning the blades off, timing is started with a stop watch, and at the same time the foam height read in mm. from the 100 ml. mark. The foam half-life is defined as the time it takes for liquid to drain out of the foam and reach the 50 ml. mark. The results were as follows:

Table 5

| Product | Solution Clarity | Foam Height in mm | Half Life in sec. |
|---|---|---|---|
| (a) | Clear | 0 | 0 |
| (b) | Clear | 0 | 0 |

Table 5-continued

| Product | Solution Clarity | Foam Height in mm | Half Life in sec. |
|---|---|---|---|
| (c) | Clear | 0 | 0 |
| (d) | Clear | 0 | 0 |
| (e) | Clear | 0 | 0 |
| (f) | Clear | 0 | 0 |

Another test was made using the "Cylinder Shake Test", the procedure of which follows:

100 ml. of test solution is gently poured down the walls of a 250 ml. graduated cylinder that has a glass stopper. The cylinder is stoppered and inverted 20 times in 15 seconds, finally resting it in an upright position. The foam volume is read in ml. from the base of the foam. The test results were as follows:

Table 6

| (a) | Clear | 0 | 0 | 0 |
| (b) | Clear | 0 | 0 | 0 |
| (c) | Clear | 0 | 0 | 0 |
| (d) | Clear | 0 | 0 | 0 |
| (e) | Clear | 0 | 0 | 0 |
| (f) | Clear | 0 | 0 | 0 |

All three tests for foaming properties show that the products tested were non-foaming.

A typical cosmetic emulsion, utilizable as a hand cream or baby lotion, which contains a product of this invention is prepared as follows:

Example 7

| Component | % by Wt. |
|---|---|
| Mineral Oil (65/75 Visc.) | 35.0 |
| Lanolin (Cosmetic Grade) | 1.0 |
| Cetyl Alcohol | 1.0 |
| "Tween 80" (Atlas Powder Co.) (non-ionic emulsifiers) | 5.4 |
| "Span 80" (Atlas Powder Co.) (non-ionic emulsifiers) | 2.6 |
| Product of Example 3 | 0.2 |
| Water (Distilled) | 54.8 |

This composition was prepared as follows: The mineral oil, lanolin, cetyl alcohol, "Tween 80", and "Span 80" were combined and heated to about 65°–70° C. The water and Product of Example 3 were combined and heated to about 65°–70° C. Then the hot aqueous solution was added slowly to the hot non-aqueous phase while stirring, and agitation was maintained until emulsification was effected. Then the emulsion was cooled with continued stirring to room temperature. The result product was an oil-in-water emulsion.

The above cosmetic composition comprises an oil-in-water emulsion but it is within the scope of the present invention to use water-in-oil emulsions for the same purposes.

The invention claimed is:

1. A method of controlling the proliferation of bacteria which comprises applying to said bacteria an effective amount to inhibit said bacteria of a product formed by the condensation of 1,4-di-halo-2-butene and a difunctional tertiary amine, said difunctional tertiary amine being selected from the group consisting of di-lower-alkyl piperazine, 1,4-diazabicyclo (2.2.2) octane, and an amine of the formula:

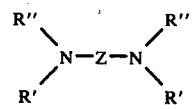

wherein Z is a divalent aliphatic radical of 2 to 10 carbon atoms containing from 0 to 2 double bonds and from 0 to 2 hydroxy substituents and wherein R' and R" are part of a heterocyclic group when combined with N, said heterocyclic group being selected from the group consisting of N-piperidino, N-pyrrolidino, N-morpholino and N-homopiperidino.

2. The method of claim 1 wherein the 1,4-dihalo-2-butene is selected from the group consisting of 1,4-dichloro-2-butene and 1,4-dibromo-2-butene.

3. The method of claim 1 wherein said bacteria are in aqueous media.

* * * * *